United States Patent
Herbst et al.

[11] Patent Number: 6,021,347
[45] Date of Patent: Feb. 1, 2000

[54] ELECTROCHEMICAL TREATMENT OF MALIGNANT TUMORS

[76] Inventors: Ewa Herbst, P.O. Box 89, Edgewater, N.J. 07020; Benedict Aurian-Blajeni, 68 Blackstone St., Bellingham, Mass. 02019

[21] Appl. No.: 08/985,287

[22] Filed: Dec. 4, 1997

Related U.S. Application Data

[60] Provisional application No. 60/033,223, Dec. 4, 1996.

[51] Int. Cl.$^7$ ........................................................ A61N 1/08
[52] U.S. Cl. .............................. 607/2; 128/898; 607/88; 607/104
[58] Field of Search .......................... 607/2, 3, 88, 104; 604/20, 21; 128/898

[56] References Cited

U.S. PATENT DOCUMENTS

| | | | |
|---|---|---|---|
| 4,289,135 | 9/1981 | Nordenstrom et al. | 607/62 |
| 4,846,950 | 7/1989 | Yao et al. | 604/20 |
| 5,005,588 | 4/1991 | Rubin | 604/20 |
| 5,028,594 | 7/1991 | Carson | 514/23 |
| 5,360,440 | 11/1994 | Andersen | 607/116 |
| 5,368,841 | 11/1994 | Trauner et al. | 424/9 |
| 5,458,627 | 10/1995 | Baranowski et al. | 607/51 |
| 5,468,223 | 11/1995 | Mir | 604/20 |
| 5,674,267 | 10/1997 | Mir et al. | 607/72 |
| 5,718,246 | 2/1998 | Vona | 128/898 |

*Primary Examiner*—Jeffrey R. Jastrzab
*Attorney, Agent, or Firm*—Michael Ebert

[57] ABSTRACT

A technique and apparatus therefor adapted to treat in situ a malignant tumor, use being made of a working electrode and a counterelectrode implanted in the tumor at spaced positions. Applied across the electrodes is a voltage causing a direct current to flow through the tumor producing an electrochemical reaction yielding multiple reaction products, some of which are cytotoxic agents destructive of cancer cells. Coupled to the electrodes is a control unit which acts to regulate the voltage applied thereto so as to optimize the yield of those cytotoxic agents having the greatest efficacy.

11 Claims, 1 Drawing Sheet

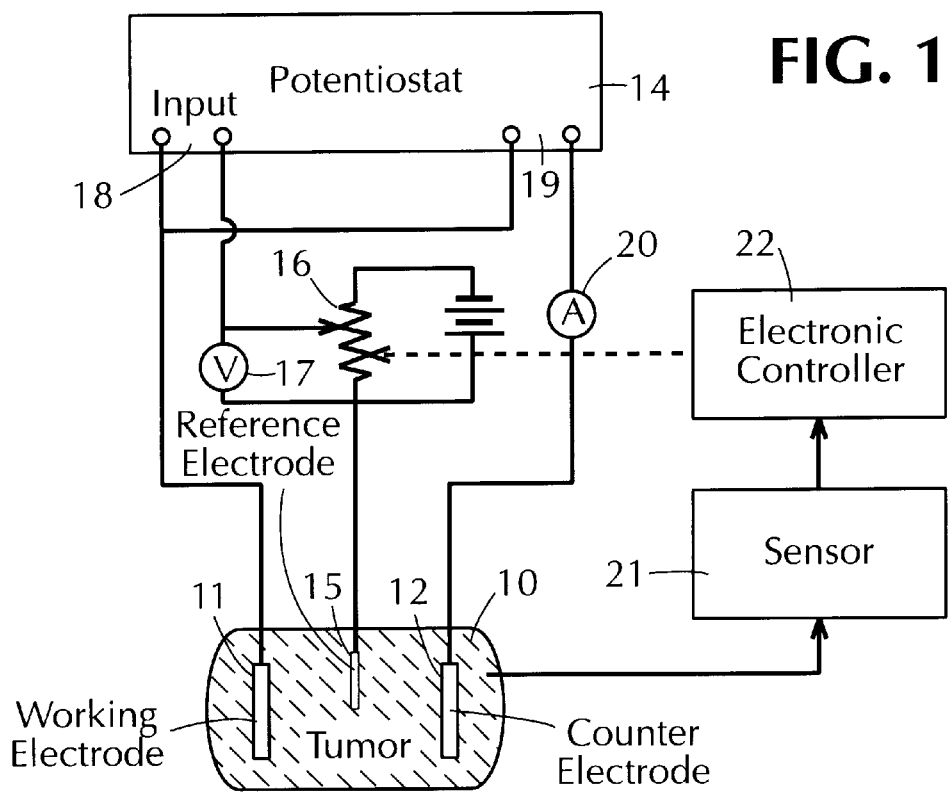
FIG. 1
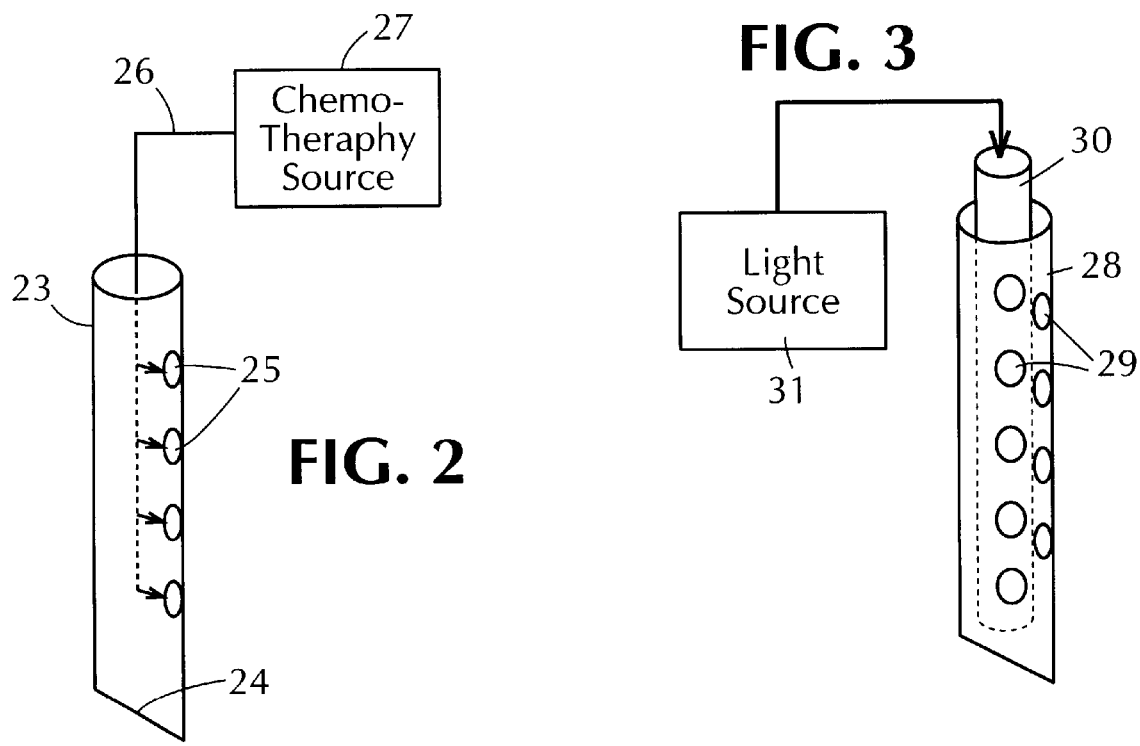
FIG. 2
FIG. 3

ELECTROCHEMICAL TREATMENT OF MALIGNANT TUMORS

RELATED APPLICATIONS

This application is related to our provisional application Ser. No. 60/033,223, filed Dec. 4, 1996, entitled "Method, Process and Apparatus for Electrical, Chemical, Electrochemical and/or Photochemical Stimulation of Biological and Biotechnological Processes," the entire disclosure of which is incorporated herein by reference.

BACKGROUND OF INVENTION

1. Field of Invention

This invention relates generally to the electrochemical treatment of malignant tumors and neoplasms by applying a voltage across working and counterelectrodes implanted in the tumor to cause a direct current to flow through the tumor producing an electrochemical reaction yielding multiple reaction products some of which act as cytotoxic agents to destroy cancer cells, and more particularly to a treatment of this type in which the voltage applied to the electrodes is regulated to maintain it at a value which optimizes the yield of those cytotoxic agents having the greatest efficacy.

2. Status of Prior Art

Oncology is the branch of medical science dealing with tumors. The concern of the present invention is with tumors and other forms of neoplasm which are malignant and therefore cancerous. The distinction between a benign and a malignant tumor is that the latter will invade surrounding tissues and spread or metastasize to other sites, whereas a benign tumor will not spread.

The common practice in the field of oncology to cure or ameliorate a cancerous condition is by appropriate surgery, radiotherapy or chemotherapy, sometimes used singly, but more often in combination.

Radiotherapy which produces its biologic effect on cancerous tissue by ionization is carried out by megavolt energy radiation in the form of X-rays from a linear accelerator or gamma rays from a cobalt 60 source. Radiation is highly penetrating, but in order to reach the region of the tumor being treated, the radiation beam must pass through regions containing healthy tissue and may therefore destroy these as well as the malignant tumor.

Chemotherapy dictates the utmost care in monitoring and controlling the administration of cytotoxic drugs, for the biochemistries of malignant and non-malignant cells are so similar that it is difficult to destroy cancerous cells without concurrently destroying healthy cells. The adverse effects of chemotherapy are notorious.

It is also known to destroy malignant tumors by elevating the temperature of the tumor to a level at which cancerous cells are destroyed. One method used for this purpose is to focus a beam of microwave energy of the type generated in a microwave oven onto the tumor. But the drawback of this technique is that healthy tissues through which the beam must pass to reach the tumor have a higher moisture content than the interior of the tumor and are therefore more reactive to microwave energy.

The problem with surgery to excise a malignant tumor is that the location of the tumor, as in the case of a tumor in the brain, may be such as to render the tumor inoperable. But even where the tumor is accessible to the surgeon's scalpel, then in order to reach this tumor, one must cut through and damage healthy tissue. Moreover with surgery, one cannot be sure that all malignant cells have been removed, and the residual cells may metastasize.

The primary concern of the present invention is with in situ electrochemical treatment of a malignant tumor, the treatment acting to destroy the tumor without damaging regions surrounding the tumor. Such electrochemical treatment of tumors is now referred to in the medical literature as ECT.

In an ECT procedure, electrodes are implanted at spaced positions in or around the malignant tumor to be treated. Applied across these electrodes is a low d-c voltage usually having a magnitude of less than 10 volts, causing a current to flow between the electrodes through the tumor. Due to an electrochemical reaction, reaction products are yielded which include cytotoxic agents that act to destroy the tumor.

In the ECT technique disclosed by Li et al., in Bioelectromagnetic 18:2–7 (1997), in the article "Effects of Direct Current on Dog Liver: Possible Mechanisms For Tumor Electrochemical Treatment" two platinum anode and cathode electrodes were inserted in a dog's liver with a 3 cm separation therebetween. Applied across these electrodes was a d-c voltage of 8.5 volts, giving rise to an average current through the liver of 30 mA. This was continued for 69 minutes, with a total charge of 124 coulombs.

The concentration of selected ions near the anode and cathode were measured. The concentration of $Na^+$ and $K^+$ ions were found to be higher around the cathode, whereas the concentration of $Cl^-$ ions was higher around the anode. Water content and pH were determined near the anode and cathode, the pH values being 2.1 near the anode and 12.9 near the cathode. The released gases were identified as chlorine at the anode and hydrogen at the cathode. The series of electrochemical reactions which took place during ECT resulted in the rapid and complete destruction of both normal and tumor cells in the liver.

Another example of ECT appears in the article "Electrochemical Treatment of Lung Cancer" by Xin et al. in Bioelectromagnetics 18:8–13 (1997). In this ECT procedure platinum electrodes were inserted transcutaneously into the tumor, the voltage applied thereto being in the 6–8 volt range, the current being in the 40 to 100 mA range, and the electric charge, 100 coulombs per cm of tumor diameter.

According to this article, the clinical results indicate that ECT provides a simple, safe and effective way of treating lung cancers that are surgically inoperable and are not responsive to chemotherapy or radiotherapy.

Also disclosing an ECT technique is the patent to Andersen U.S. Pat. No. 5,360,440 "In Situ Apparatus For Generating An Electrical Current in a Biological Environment."

Electrochemical reactions as a function of pH and electrode potential can be predicted by means of a Pourbaix diagram, as disclosed in the Atlas of Electrochemical Equilibria in Aqueous Solutions—Pergamon Press, 1986—by Pourbaix.

While the U.S. Pat. No. 5,458,627 of Baranowski Jr. et al. does not relate to ECT but to the electrochemically controlled stimulation of osteogenesis, it is nevertheless of prior art interest, for it discloses that reaction products produced by an electrochemical reaction includes not only hydrogen and oxygen, but also hydrogen peroxide.

In the text Methods in Cell Biology, Vol. 46—Cell Death—published by Academic Press, it is noted (page 163), that hydrogen peroxide has been reported to be an inducer of cell death in various cell systems. This type of cell death is attributed to the direct cytotoxicity of $H_2O_2$ and other oxidant species generated from $H_2O_2$.

SUMMARY OF INVENTION

In view of the foregoing, the main object of this invention is to provide an electrochemical technique and apparatus for carrying out this technique adapted to treat, in situ, a malignant tumor or other form of neoplasm to destroy cancerous tissues.

A significant feature of this treatment in which a voltage is applied across working and counterelectrodes implanted in or otherwise applied to the tumor being treated is that the voltage is controlled during electrochemical reactions produced in the malignant tumor to optimize the yield of those reaction products which act as cytotoxic agents destructive of cancerous cells.

Also an object of this invention is to provide apparatus for carrying out an ECT procedure concurrently with chemotherapy treatment to subject the malignant tumor being treated to cytotoxic chemicals from a chemotherapy source as well as from reaction products yielded by an electrochemical reaction.

Yet another object of this invention is to provide an apparatus for carrying out an ECT procedure in conjunction with photochemically-activated drugs delivered to the malignant tumor whereby as current passes through the tumor to produce an electrochemical reaction, the tumor is at the same time exposed to light rays to activate the drugs.

Briefly stated, these objects are attained by a technique and apparatus therefor adapted to treat in situ a malignant tumor, use being made of a working electrode and a counterelectrode implanted in the tumor at spaced positions. Applied across the electrodes is a d-c voltage causing a direct current to flow through the tumor producing an electrochemical reaction yielding multiple reaction products, some of which are cytotoxic agents destructive of cancer cells. Coupled to the electrodes is a control unit which acts to regulate the voltage applied thereto so as to optimize the yield of those cytotoxic agents having the greatest efficacy.

BRIEF DESCRIPTION OF DRAWING

For a better understanding of the invention, as well as other objects and further features thereof, reference is made to the following detailed description to be read in conjunction with the accompanying drawing, wherein:

FIG. 1 is a schematic diagram of an electrochemical treatment system (ECT) in accordance with the invention for destroying a malignant tumor or other form of neoplasm;

FIG. 2 illustrates an electrode included in an ECT system adapted to deliver a chemotherapy drug to the tumor being treated; and FIG. 3 illustrates an electrode to be included in an ECT system adapted to apply light energy to a tumor being treated.

DETAILED DESCRIPTION OF INVENTION

Shown in FIG. 1 is an ECT system in accordance with the invention for treating a malignant tumor 10. The treatment is carried out in situ by passing a direct electrical current through the tumor to produce an electrochemical reaction therein yielding multiple reaction products some of which have cytotoxic properties. The electrochemistry of the tumor depends on its organic nature. Thus the organic solutions permeating a cancerous liver are somewhat different from those found in a cancerous pancreas.

Typical reaction products resulting from passing direct current through tissues are hydrogen and oxygen, as well as chlorine and hydrogen peroxide. Hydrogen peroxide which is a highly probable intermediate is known to have strong cytotoxic properties, whereas other reaction products yielded in an ECT procedure vary in their effectiveness in destroying cancer cells. In an ECT system in accordance with the invention, the system operates to optimize the yield of those reaction products that have the greatest ability to destroy cancer cells.

In the system shown in FIG. 1 there are implanted in tumor 10 a working electrode 11 and spaced therefrom, a counterelectrode 12. These electrodes may be formed of platinum or other noble metals or alloys thereof. Or the electrodes may be formed of high-strength, non-reactive metals, such as titanium and stainless steel. Electrodes made of conductive oxides and semiconductors can also be used.

In practice, the electrodes, especially the counterlectrodes, are preferably fabricated of porous material to enlarge their effective surface area and thereby reduce the current density per unit crossectional area of the electrode. Also more than one counterlectrode can be used in conjunction with one working electrode in order to distribute current flow throughout the tumor.

Applied across electrode 11 and 12 to cause a current to flow through the regions of the tumor bridging these electrodes is a voltage derived from a battery or other d-c voltage source 13 under the control of a potentiostat 14.

A potentiostat is an instrument used in an electrochemical process which is adapted to automatically control the potential of a test or working electrode to within certain limits during an electrochemical reaction. Potentiostat 14 in the system disclosed in FIG. 1 acts to govern the d-c voltage derived from battery 13 which is applied to working electrode 11 so that the multiple reaction products yielded by the electrochemical reaction when current passes through tumor 10, include products which have the cytotoxic properties most effective in destroying cancer cells.

Potentiostat 14 maintains at a substantially constant level the potential difference between working electrode 11 and the electrochemical solution in tumor 10 (the working electrode potential) with respect to a reference electrode 15. Reference electrode 15 is implanted in the tumor as close as possible to the working electrode 11.

The biologic cell created by working electrode 11 and reference electrode 15 implanted in the tissue of the tumor is connected in series with a potentiometer 16. A voltmeter 17 is connected between the variable tap on potentiometer 16 and one end of battery 13 whose other end is connected through the resistance of potentiometer 16 to reference electrode 16. The circuit of the cell is completed through input 18 of potentiostat 14.

Potentiometer 16 is adjusted by means of voltmeter 17 to obtain the required electromotive force (EMF) which is equal and opposite to the desired working electrode-reference electrode EMF. Output 19 of the potentiostat, via ammeter 20 and counterelectrode 12, feeds a current to working electrode 11 appropriate to its electrode potential. As this potential varies during the electrochemical reaction and thereby alters the EMF of the original cell, the voltage developed at the input 18 of this potentiostat is not zero, but constitutes an error signal. This signal operates the electronic feedback to give an output that restores the desired electrode potential.

The potential to be maintained on working electrode 11 by potentiostat 14 is that potential which, for the tumor being treated, gives rise to a current flow through the tumor that produces an electrochemical reaction therein yielding those reaction products which includes cytotoxic agents having the greatest ability to destroy cancer cells.

For example, if it is determined empirically that the volume of hydrogen peroxide, a highly effective cytotoxic agent, included in the multiple reaction products yielded by the electrochemical reaction reaches its higher level when the potential on the working electrode is in a 1.00 to 1.25 volt range, then the potentiostat system is adjusted to maintain the potential in this range. Or the potentiostatic system operates in whatever other range yields reaction products having optimal cytotoxic characteristics.

The adjustable potentiometer 16 makes it possible to operate the system manually. In order to operate the system so that it automatically maintains the voltage in the desired range with respect to a selected variable in the electrochemical process indicative of the desired cytotoxic reaction products being generated, this variable is sensed by a sensor 21. The variable being sensed may simply be the pH in the vicinity of the counterelectrode or at the working electrode.

Sensor 21 produces an electrical signal that depends on the variable being sensed, this signal being applied to an electronic controller 22 which compares the signal with a set point signal to produce an error signal that depends on the deviation of the sensor signal from the set point; that is the extent to which the sensed pH deviates from the pH value that reflects an optimum condition.

Controller 22 is coupled to potentiometer 16 in the potentiostat system, acting to adjust the voltage to maintain the desired voltage at which the ECT system is most effective in destroying cancer cells. In practice, one may dispense with the potentiostat, and use the electronic controller to regulate the voltage applied to the electrodes.

To minimize polarization at the electrodes of the electrochemical system, the polarity of the voltage applied to the electrodes may on occasion be reversed, in which case the counterelectrode becomes the working electrode. And the direct voltage applied to the electrodes need not be continuous, but may be pulsed or undulatory.

Electrodes

The nature of the electrodes must be appropriate to the tumor or other form of neoplasm being treated. Thus in the case of skin cancer, the electrodes must then be applied to the skin surface, and for this purpose flexible patch electrodes are suitable. In the case of tumors in which the electrodes are to be implanted, the appropriate electrodes depend on the character of the tumor. Thus with a soft tumor, the electrode may take the form of a flexible pin capable of penetrating the tumor, whereas for relatively hard tumors, a screw-type electrode may be preferable.

In some instances it may be desirable to combine chemotherapy with an ECT procedure either concurrently or alternately. For this purpose, as shown in FIG. 2, either the working electrode or the counterelectrode may take the form of a hollow tubular metal electrode 23 having a cutting tip 24 to facilitate its insertion in a tumor.

Electrode 23 is provided with a series of apertures 25 along its length. Delivered through a suitable line 26 feeding electrode 23 is a flowable drug from a chemotherapy source 27. Hence in this arrangement, the tumor is subjected to a cytotoxic agent derived from a chemotherapy source as well as cytotoxic agents yielded by the electrochemical ECT process.

In treating a malignant tumor it is vital that no portion thereof remains untreated, for untreated residual tissue may spread with serious consequences. By combining chemotherapy with an ECT procedure, one is then able to ensure fuller treatment of the tumor.

Another approach to combining chemotherapy with an ECT procedure is to use a photochemically activated drug which is absorbed by the tumor, or delivered thereto through the electrodes, but until such time as it is activated by light energy, remains inactive and innocuous.

For this purpose, the metal electrode 28, as shown in FIG. 3 is hollow and has myriad apertures 29 which are circumferentially distributed. Received within the hollow electrode is a flexible fiber optics light pipe 30 which is coupled to an external high-intensity light source 31.

Thus when the tumor impregnated with the light-activatable drug undergoes an ECT procedure, the tumor is at the same time (or in alternate sessions) subjected to light energy to activate the drug, thereby releasing cytotoxic agents whose activity is combined with the agents released as reaction products.

While there has been shown and described preferred embodiments of an electrochemical treatment of malignant tumors in accordance with the invention, it will be appreciated that many changes may be made therein within the spirit of the invention. Thus while we have disclosed means to regulate the voltage applied to the electrodes, in lieu thereof, use may be made of means to regulate the current flowing through the tumor to optimize the yield of cytotoxic agents having the greatest efficacy.

We claim:

1. Apparatus for subjecting a tumor or other neoplasm in situ to electrochemical treatment to destroy the tumor, said apparatus comprising:

A. a working electrode and a counterelectrode, the electrodes being adapted to be attached at spaced positions to the tumor or its vicinity;

B. means for applying a voltage across the electrodes to cause a current to flow through the tumor producing an electrochemical reaction yielding multiple reaction products at least one of which is a cytotoxic agent capable of destroying the neoplasm; and C. means to regulate the voltage applied to said electrodes to maintain it at a value which optimizes the yield of said cytotoxic agent.

2. Apparatus as set forth in claim 1, in which the electrodes are implanted in the tumor.

3. Apparatus as set forth in claim 1, in which the neoplasm is on a skin surface and said electrodes are attached to the skin surface.

4. Apparatus as set forth in claim 1, further including an external source of a flowable cytotoxic agent, wherein at least one of the electrodes is hollow and provided with openings through which said flowable cytotoxic agent is fed to be discharged into the tumor.

5. Apparatus as set forth in claim 1, further including means for impregnating the tumor is with a photoactivated cytotoxic drug, and at least one of the electrodes is hollow and provided with a circumferential array of apertures from which light, from a fiber optics pipe inserted in the electrode, is discharged into the tumor to activate the drug.

6. Apparatus as set forth in claim 1, in which said means to regulate the voltage includes a reference electrode implanted in the tumor adjacent the working electrode.

7. Apparatus as set forth in claim 6, further including a potentiostat coupled to said reference electrode to maintain the potential on said working electrode at a constant level.

8. Apparatus as set forth in claim 7, in which the potentiostat has an input coupled to a d-c source through a potentiometer which is adjustable to vary the potential of the working electrode applied thereto by an output of the potentiostat.

9. Apparatus as set forth in claim 1, further including means to sense a variable in the electrochemical reaction that reflects the yield of said cytotoxic agent to produce a signal, and an electronic controller to which the signal is applied to automatically regulate the voltage applied to the electrodes to optimize said yield.

10. A method for destroying a tumor or other neoplasm comprising the steps of:

A. applying a voltage to electrodes attached to the tumor or adjacent thereto to cause a current to flow through the tumor to produce an electrochemical reaction yielding multiple reaction products, at least one of which is a cytotoxic agent that is capable of destroying the neoplasm; and B. regulating said voltage to maintain it at a value which optimizes the yield of said cytotoxic agent.

11. A method as set forth in claim 10, in which the electrodes are formed of platinum.

* * * * *